(12) United States Patent
Zhuang et al.

(10) Patent No.: US 9,792,823 B2
(45) Date of Patent: Oct. 17, 2017

(54) MULTI-VIEW LEARNING IN DETECTION OF PSYCHOLOGICAL STATES

(71) Applicant: Raytheon BBN Technologies Corporation, Cambridge, MA (US)

(72) Inventors: Xiaodan Zhuang, Somerville, MA (US); Viktor Rozgic, Boston, MA (US); Michael Roger Crystal, West Newton, MA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 485 days.

(21) Appl. No.: 14/486,447

(22) Filed: Sep. 15, 2014

(65) Prior Publication Data

US 2016/0078771 A1 Mar. 17, 2016

(51) Int. Cl.
*G09B 5/00* (2006.01)
*A61B 5/16* (2006.01)
*G10L 25/63* (2013.01)

(52) U.S. Cl.
CPC ............... *G09B 5/00* (2013.01); *A61B 5/165* (2013.01); *G10L 25/63* (2013.01)

(58) Field of Classification Search
CPC ........... G09B 5/00; A61B 5/165; G10L 25/63; G06N 5/02; G06N 5/04
USPC .......................................................... 706/46
See application file for complete search history.

(56) References Cited

U.S. PATENT DOCUMENTS

| | | | | |
|---|---|---|---|---|
| 2003/0200040 A1* | 10/2003 | Trygg | ................. | G01N 21/359 702/85 |
| 2004/0210159 A1* | 10/2004 | Kibar | ................. | A61B 5/4803 600/558 |
| 2005/0228236 A1* | 10/2005 | Diederich | ............ | A61B 5/7267 600/300 |
| 2008/0221401 A1* | 9/2008 | Derchak | ................. | A61B 5/16 600/301 |
| 2011/0245633 A1* | 10/2011 | Goldberg | ............... | A61B 5/681 600/301 |
| 2014/0114655 A1* | 4/2014 | Kalinli-Akbacak | .... | G10L 25/63 704/231 |
| 2014/0330089 A1* | 11/2014 | Webb | ................. | A61B 5/02405 600/301 |
| 2014/0358539 A1* | 12/2014 | Rao | ........................ | G10L 15/063 704/243 |

OTHER PUBLICATIONS

Xu C. et al., "A Survey on Multi-view Learning", Apr. 2013.*
(Continued)

*Primary Examiner* — Dave Misir
(74) *Attorney, Agent, or Firm* — Daly, Crowley, Mofford & Durkee, LLP (57) ABSTRACT

Systems and methods for using multi-view learning to leverage highly informative, high-cost, psychophysiological data collected in a laboratory setting, to improve post-traumatic stress disorder (PTSD) screening in the field, where only less-informative, low-cost, speech data are available. Partial least squares (PLS) methods can be used to learn a bilinear factor model, which projects speech and EEG responses onto latent spaces, where the covariance between the projections is maximized. The systems and methods use a speech representation based on a combination of audio and language descriptors extracted from spoken responses to open-ended questions.

17 Claims, 7 Drawing Sheets

(56) References Cited

OTHER PUBLICATIONS

Wold S. et al., "The PLS method—partial least squares projections to latent structures—and its applications in industrial RDP (research, development, and production).", Jun. 2004.*

Wold S. et al., "Principal Component Analysis", Chemometrics and Intelligent Laboratory Systems, 2, 1987, pp. 37-52.*

Lampert C. et al., "Weakly-Paired Maximum Covariance Analysis for Multimodal Dimensionality Reduction and Transfer Learning", 2010.*

Gonen et al.; "Multiple Kernel Learning Algorithms:" Journal of Machine Learning Research 12 (2011); Jul. 2011; pp. 2211 to 2268.

Blum et al.; "Combining Labeled and Unlabeled Data with Co-Training;" COLT' 98 Proceedings of the eleventh annual conference on Computational learning theory; Jan. 1998; 10 Pages.

Quadrianto et al.; "Learning Multi-View Neighborhood Preserving Projections;" Proceedings of the 28th International Conference on Machine Learning; Jun. 28, 2011; 8 Pages.

Arora et al.; "Muiti-View CCA-Based Acoustic Features for Phonetic Recognition Across Speakers and Domains;" Proceedings of the 38th International Conference on Acoustics, Speech and Signal Processing; Jan. 2013; 5 Pages.

Sridharan et al.; "An Information Theoretic Framework for Multi-View Learning;" Proceedings of the 21st Annual Conference on Learning Theory; Jul. 9, 2008; 12 Pages.

Livescu et al.; "Multi-View Learning of Acoustic Features for Speaker Recognition;" Automatic Speech Recognition and Understanding Workshop; Jan. 2009; 4 Pages.

Dehak et al., "Front-End Factor Analysis for Speaker Verification;" Proceedings of the IEEE Transactions on Audio, Speech, and Language Processing, vol. 19, No. 4; May 2011; 11 Pages.

Kenny et al., "Eigenvoice Modeling with Sparse Training Data;" Proceedings of the IEEE Transactions on Speech and Audio Processing, vol. 13, No. 3; May 2005; 10 Pages.

Wegelin, "A Survey of Partial Least Squares (PLS) Methods, with Emphasis on the Two-Block Case;" Technical Report No. 371; Department of Statistics at the University of Washington; Mar. 2000; 46 Pages.

\* cited by examiner

MULTI-VIEW LEARNING IN DETECTION OF PSYCHOLOGICAL STATES

STATEMENT REGARDING FEDERALLY SPONSORED RESEARCH

This invention was made with Government support under Contract N666001-11-C-4006 awarded by the Defense Advance Research Project Agency (DARPA) and Space and Naval Warfare Systems Center Pacific. The Government has certain rights in the invention.

BACKGROUND

Post-traumatic stress disorder (PTSD) is a debilitating condition resulting from trauma exposure that involves persistent trauma-related thoughts and nightmares, avoidance of trauma-related stimuli, distorted beliefs about oneself or others, distorted cognitions about the cause of the trauma, sleep disturbance, and irritable behavior or angry outbursts.

Mental healthcare providers need assessment methods that reliably and accurately determine PTSD diagnostic status, especially among veterans and military personnel who are seeking treatment for the disorder in record numbers. Currently, standardized diagnostic interviews, such as the Structured Clinical Interview for the DSM-IV (SCID) and the Clinician-Administered PTSD Scale (CAPS), are the gold standard for determining PTSD diagnostic status. However, in order to best differentiate PTSD from similar psychiatric disorders and to address potential response bias, multimethod assessment procedures that incorporate standardized diagnostic interviews, self-reports, psychophysiological assessment, and other methods are recommended.

Advances in psychophysiological signal processing and machine learning techniques, together with more affordable sensors (e.g., electroencephalography (EEG)), show improved screening performance relative to structured interviews. In particular, a growing body of work proposes machine learning approaches for assessing psychological health disorders such as PTSD, depression, and mild Traumatic Brain Injury (mTBI), using modalities including heart rate, heart rate with galvanic skin response (GSR), EEG, electrocardiography (EKG), voice quality, speech, speech in dialog systems, and modality combinations.

Psychophysiological responses to structured protocols carry relevant information for psychological health disorder classification, and the combination of psychophysiological and audio-visual features can improve disorder detection rates relative to using audio-visual features alone. The impact of this result is diminished in real world applications because psychophysiological sensors (i.e., EEG, GSR, and EKG) generally are more resource intensive to apply and more aversive to patients than non-intrusive sensors (i.e., audio and video recording), thus decreasing engagement rates.

SUMMARY

It is appreciated herein that the performance of post-traumatic stress disorder (PTSD) detection can be improved by training models that exploit multi-view learning applied to electroencephalography (EEG) and speech-based data. The trained models allow PTSD detection when only speech responses obtained through a non-aversive protocol are available for diagnostic classification.

According to one aspect, a system for detecting psychological states comprises a device to obtain sensor data corresponding to a subject's response to stimuli; a feature extraction processor to extract one or more features from the sensor data to generate feature representation data, the feature representation data being associated with a first view; a memory device configured to store a projection matrix modeling a relationship between the first view and a second view, and to store a detection model trained using training data associated with the first view transformed to a latent space using the projection matrix; and a detection module to transform the feature representation data to the latent space using the projection matrix, and to apply the transformed feature representation data to the detection model to detect one or more psychological states of the subject. In some embodiments, the one or more psychological states include post-traumatic stress disorder (PTSD) indicators.

In various embodiments, the sensor data comprises audio signal data responsive to the subject's speech, the feature representation data comprises an audio representation and a language representation. The feature extraction processor may comprise a frame-level feature extraction processor to receive the audio signal data and to generate frame-level feature vectors; an audio feature extraction processor to generate the audio representation using the frame-level feature vectors; an automatic speech recognition (ASR) processor to apply a speech recognizer to the frame-level feature vectors to transcribe the speech responses; and a distress indicator extraction processor to extract psychological distress indicators from the transcribed speech responses to generate the language representation.

In certain embodiments, the second view is associated with psychophysiological data (e.g., electroencephalography (EEG) data). In some embodiments, the stimuli include images stored upon a non-volatile memory, the system further comprising a computer display to display the images. In a particular embodiment, the projection matrix comprises a bilinear factor model selected to maximize the covariance between the first and second views.

The system may further include components to train the psychological user state detection model. Here, the device to obtain sensor data comprises a first device to obtain first sensor data corresponding to a training subject's response to the stimuli and a second device to obtain second sensor data corresponding to the training subject's response to the stimuli, wherein the feature extraction processor is a first feature extraction processor. The system may further comprise a second feature extraction processor to extract one or more features from the second sensor data to generate second feature representation data, the second feature representation data being associated with a second view; a relationship learning module to receive the first and second feature representation data and to learn the projection matrix for projecting the first feature representation to a latent space related to the first and second views; and a training module to transform the feature representation data to the latent space using the projection matrix, and to train the psychological user state detection model using the transformed feature representation data. In some embodiments, the first sensor data comprises audio signal data and the second sensor data comprises psychophysiological data.

According to another aspect, a method for detecting psychological states comprises obtaining sensor data associated with a first view, the sensor data corresponding to a subject's response to stimuli; performing feature extraction to generate feature representation data; transforming the feature representation data to a latent space using a projection matrix; and applying a detection model to the transformed feature representation data to detect one or more psychological states of the subject. In some embodiments, applying a detection model to the transformed feature representation data to detect one or more psychological states of the subject comprises detecting post-traumatic stress disorder (PTSD) indicators.

In certain embodiments, obtaining sensor data associated with a first view comprises obtaining audio signal data via a microphone. Performing feature extraction may comprise receiving the audio signal data; generating frame-level feature vectors; generating an audio representation using the frame-level feature vectors; applying an automatic speech recognition (ASR) to the frame-level feature vectors to transcribe the speech responses; and extracting psychological distress indicators from the transcribed speech responses to generate a language representation.

In particular embodiments of the method, the second view is associated with psychophysiological data (e.g., electroencephalography (EEG) data). In some embodiments, the method further comprises displaying images upon a computer display to elicit the subjects' response.

The method may further include steps to train the psychological user state detection model. Here, obtaining sensor data associated with a first view comprises obtaining first sensor data using a first device, the first sensor data corresponding to a training subject's response to the stimuli, and obtaining second sensor data using a second device, the second sensor data corresponding to the training subject's response to the stimuli. The method may further comprise performing feature extraction on the first sensor data to generate first feature representation data, the first feature representation data being associated with a first view; performing feature extraction on the second sensor data to generate second feature representation data, the second feature representation data being associated with a second view; learning the projection matrix using the first and second feature representation data; transforming the first feature representation data to the latent space using the projection matrix; and training the psychological user state detection model using the using the transformed first feature representation data.

Thus, in contrast to conventional multi-modal fusion approaches, the systems and techniques disclosed herein use a multi-view learning framework that can be used to detect PTSD using low-cost information (e.g., speech), while leveraging high-cost information (e.g., EEG signals) for training.

BRIEF DESCRIPTION OF THE DRAWINGS

The concepts, structures, and techniques sought to be protected herein may be more fully understood from the following detailed description of the drawings, in which.

The drawings are not necessarily to scale, or inclusive of all elements of a system, emphasis instead generally being placed upon illustrating the concepts, structures, and techniques sought to be protected herein.

DETAILED DESCRIPTION

Figure 1:
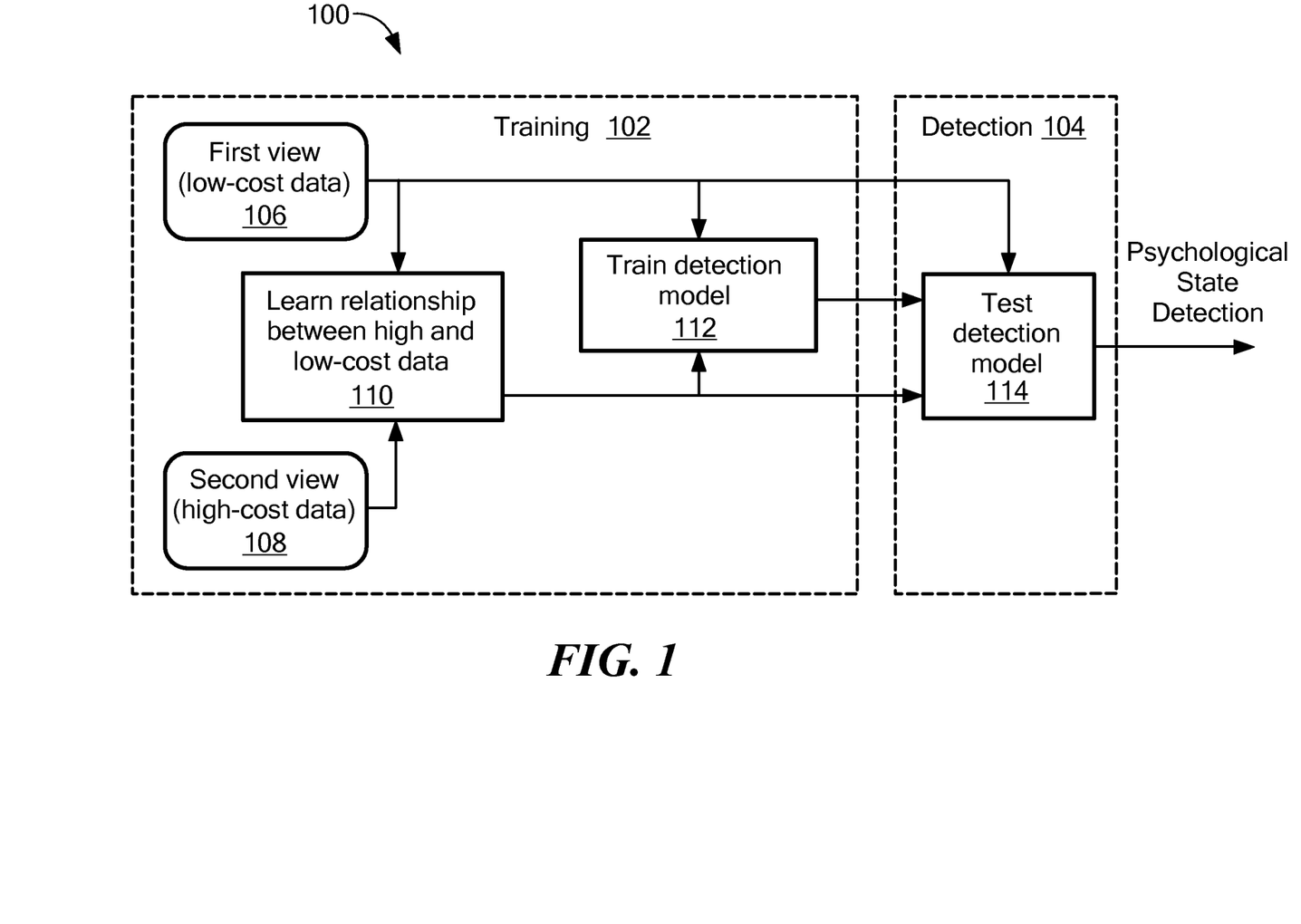
FIG. 1 is a block diagram showing an illustrative multi-view learning framework for detecting psychological states.

Referring to FIG. 1, an illustrative framework 100 includes a training portion 102 for training a multi-view model and a detection portion 104 for using the trained model to detect psychological states. The training portion may be performed in a laboratory or other controlled setting on a limited number of subjects, whereas the detection portion can be performed in the field on a broader population.

The training portion 102 uses a multi-view learning method. It will be understood that multi-view learning refers to a genre of machine learning methods that addresses heterogeneous subsets (i.e., views) of a data collection. Views can be obtained from different sources (e.g., modalities) and have different availability at various stages of machine learning. The specific multi-view learning method infers latent spaces from multi-view data at training time. This technique can improve detection performance in a scenario where the multi-view data is available only at training time. A description of this type of multi-view learning is given, for example, in Novi Quadrianto and Chistoph H Lampert, "Learning multi-view neighborhood preserving projections," in Proceedings of the $28^{th}$ International Conference on Machine Learning (ICML-11), 2011, pp. 425-432, which is hereby incorporated by reference.

Accordingly, the framework 100 utilizes a first view 106 comprising observable variables available for both training and detection, and a second view 108 comprising variables observed at training time but not available at detection time (i.e., not available within the detection portion 104). It will be understood that the framework 100 uses the second view 108 to inform the single-view testing data by modeling the fundamental relationship between the two views 106, 108. As discussed further below, the first view 106 corresponds to what is referred to herein as "low-cost" information, whereas the second view 108 corresponds to what is referred to herein as "high-cost" information. The distinction between high and low-cost information is discussed below in, conjunction with FIG. 2.

The framework training portion 102 includes a relationship-learning stage 110 to learn a structural relationship (or "model") between observed low-cost data (i.e., data associated with the first view 106) and observed high-cost data (i.e., data associated with the second view 108). In some embodiments, the relationship-learning stage 110 employs partial least squares (PLS) methods to learn a bilinear factor model by projecting both views 106, 108 to latent variables in new spaces, where their covariance is maximized. The training portion 102 further includes a training stage 112 to train the detection model using the low-cost data transformed (e.g., projected or otherwise transformed) into a latent space using the learned model. Advantageously, the training stage 112 does not rely on high-cost data, which is assumed to be unavailable at detection time.

The framework detection portion 104 includes a detection stage 114 to detect psychological states. At detection time, the learned model is used to transform (or "project") the low-cost observation data into a latent space that captures the fundamental relations between the first and second views 106, 108 (i.e., the same latent space in which the detection model was trained). The projected low-cost data can then be applied to the learned model to detect psychological states.

The multi-view learning problem can be formulated as follows:

$$X_1 = TP' + E$$

$$X_2 = UQ' + F$$

where $X_1$ is an n×m matrix composed of n training samples, each sample having m observable variables in the first view 106; $X_2$ is an n×p matrix composed of n training samples, each sample having p observable variables in the second view 108; P and Q are orthogonal loading matrices that project $X_1$ and $X_2$ to latent variable spaces T and U, both of size n×d, where d is the shared size of the two latent variable spaces; and E and F are error terms in the original spaces. In a particular embodiment, the dimensionality of the latent variable spaces is fifty.

Any suitable technique can be used to solve this model. For example, the two-blocks canonical PLS of the Wold technique can be employed to solve this model using multi-view data. A description of the Wold technique is given in Jacob A Wegelin et al., "A survey of partial least squares (pls) methods, with emphasis on the two-block case," University of Washington, Department of Statistics, Tech. Rep, 2000, which is incorporated herein by reference.

Figure 2:
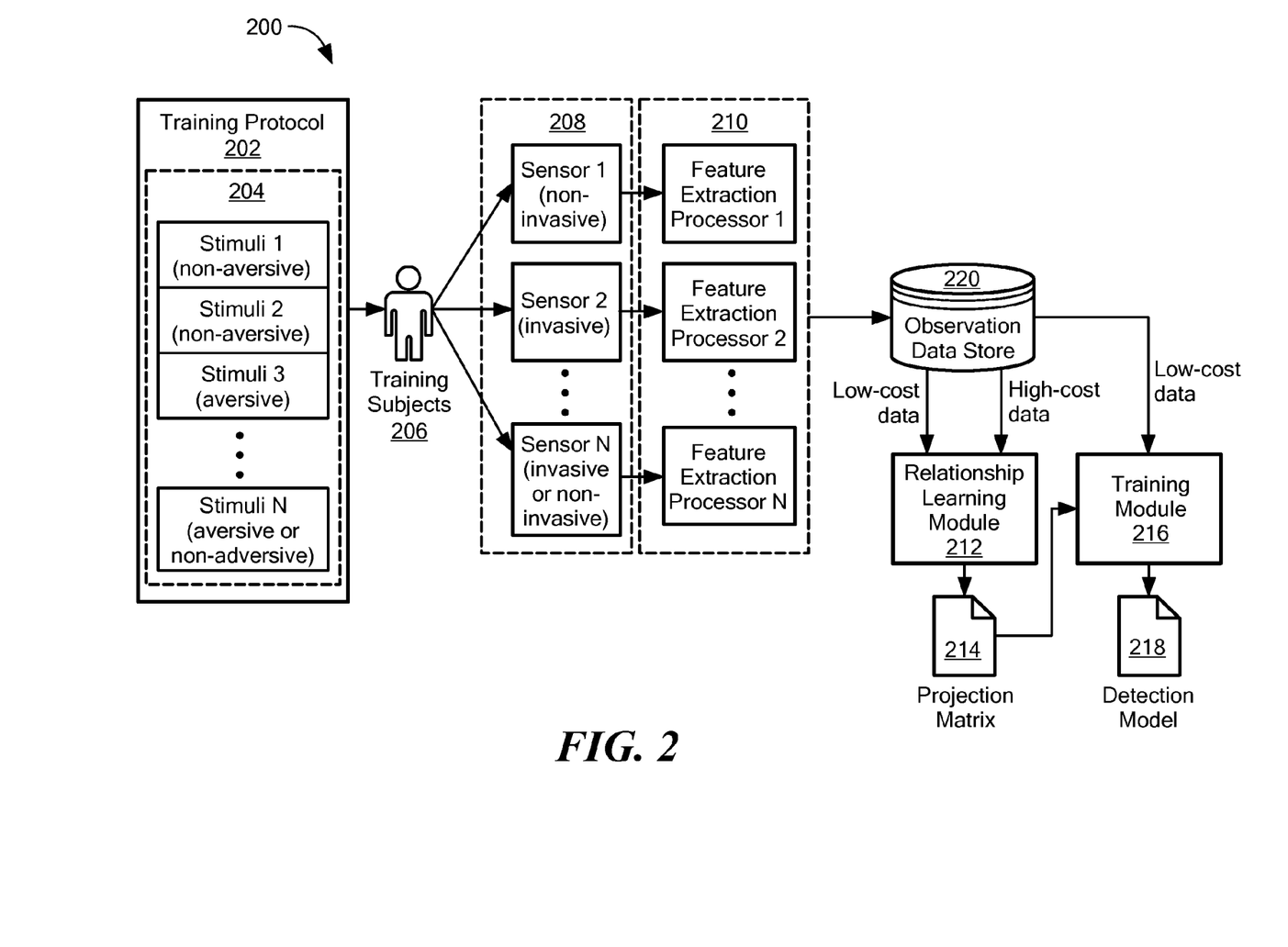
FIG. 2 is a block diagram showing an illustrative system for training a multi-view model for detecting psychological states.

FIG. 2 illustrates a system 200 for training a multi-view psychological user state detection model referred to herein as the "training system." The training system 200 includes sensors 208 operatively coupled to feature extraction processors 210, a relationship-learning module 212 operatively coupled to the feature extraction processors 210, and a training module 216 operatively coupled to the relationship learning module 212 and the feature extraction processors 210. Stimuli 204 are presented to training subjects 206 to elicit responses, which are detected, measured, recorded, or otherwise sensed by the sensors 208.

The training system 200 may be used in a controlled setting (e.g., a laboratory) wherein the subjects are generally receptive to aversive stimuli and invasive sensors (i.e., engagement rates are not a concern). Accordingly, both aversive and non-aversive stimuli 204, and both invasive and non-invasive sensors 208, are shown.

The stimuli 204 may be presented in a pre-determined sequence referred to as a data collection protocol (or more simply a "protocol") 202. The protocol 202 may also define timing dependencies between certain stimuli 202 and certain sensors 208 and/or feature extraction processors 210. In other words, the protocol can be used to synchronize stimuli and responses as needed. In certain embodiments, one or more of the stimuli are stored within a computer memory and presented to the training subjects 206 via a computer output device (e.g., a computer display or a speaker).

The stimuli 204 may include any suitable type of stimulus to elicit a response from the subject. Non-limiting examples of stimulus 208 include: generic audio, audio related to a specific trauma, generic imagery (video or still images), trauma-related imagery, multiple choice questions, open-ended questions, spoken questions, pre-recorded questions, written questions, etc. In certain embodiments, the stimuli 208 include International Affective Pictures System (IAPS) imagery. In one version of the system, an avitar talks to a person.

The sensors 208 may include any suitable type of sensor to detect, measure, record, or otherwise sense any type of response data that may be relevant to psychological states. The sensors 208 may include psychophysiological sensors, non-limiting examples of which include: electroencephalography (EEG) sensors and functional magnetic resonance imaging (fMRI) to measure brain activity; computerized tomography (CT/CAT scans); skin conductance response (SCR) and galvanic skin response (GSR) to measure skin conductance; cardiovascular sensors to measure hear rate and/or vasomotor activity; electromyography (EMG) and electrogastrogram (EGG) sensors to measure muscle activity, pupillometry sensors to measure changes in pupil diameter; electro-oculogram (EOG) and direction-of-gaze sensors to measure eye movement; impedance cardiography sensors to record cardiodynamics; electrocardiogram (EKG) sensors to measure electrical activity of the heart; and accelerometers. Other examples include a microphone to capture audio responses, a still camera to capture facial and/or body images, and a video camera to capture facial and/or body video. In some embodiments, subject responses are entered using a user input device, such as a keyboard, a mouse, or a touchscreen, any of which may correspond to sensors 208.

In a particular embodiment, audio-visual responses were recorded using a close-talk microphone and high-definition frontal face video. Psychophysiological responses include 20-channel EEG, EKG, and head motion signals recorded using the Advanced Brain Monitoring X-24 headband, and GSR signal using the Affectiva Q-sensor.

A particular protocol 202 for training a PTSD detection model includes three segments. A first segment comprises questionnaires including the Holmes-Rahe multiple life stress (MLS) inventory for quantifying stress, the Clinician Administered PTSD Scale (CAPS) for PTSD screening, and two groups of open-ended questions to describe 1) the most impactful trauma (e.g., warzone exposure) experienced by the subject, and 2) the impact it has had on the subject's emotions, behaviors, and social life. Responses to the MLS and CAPS can be mouse clicks on radio buttons and responses to the additional questions can be audio capture of subject statements. A second stimulus segment comprises positive, negative, and neutral images each drawn from the LAPS image collection. After each image is displayed for a pre-determined amount of time (e.g., five seconds), the subject is asked to state his or her thoughts about the image. A third stimulus segment comprises a sequence of images, audio clips, and/or videos specifically related to the trauma type the subject reported as having experienced personally, during the first segment. When training using subjects 206 known to be PTSD positive, the audio and video stimuli during the third segment may be skipped.

The sensors 208 are operatively coupled to one or more feature extraction processors 210, which transform raw sensor data (i.e., response data) into a reduced representational set of features (referred to herein as "feature representation data"). Transforming the input data into the set of features is called feature extraction, and typically involves reducing the dimensionality of the sensor data, discretizing it, and converting the data into feature spaces so as to be useful for learning and/or training purposes. In some embodiments, feature representation data comprises a vector of descriptors or other values. Any suitable feature extraction technique can be employed, including, but not limited to, audio and/or visual signal processing, speech analysis, and psychophysiological signal processing techniques.

Figure 4:
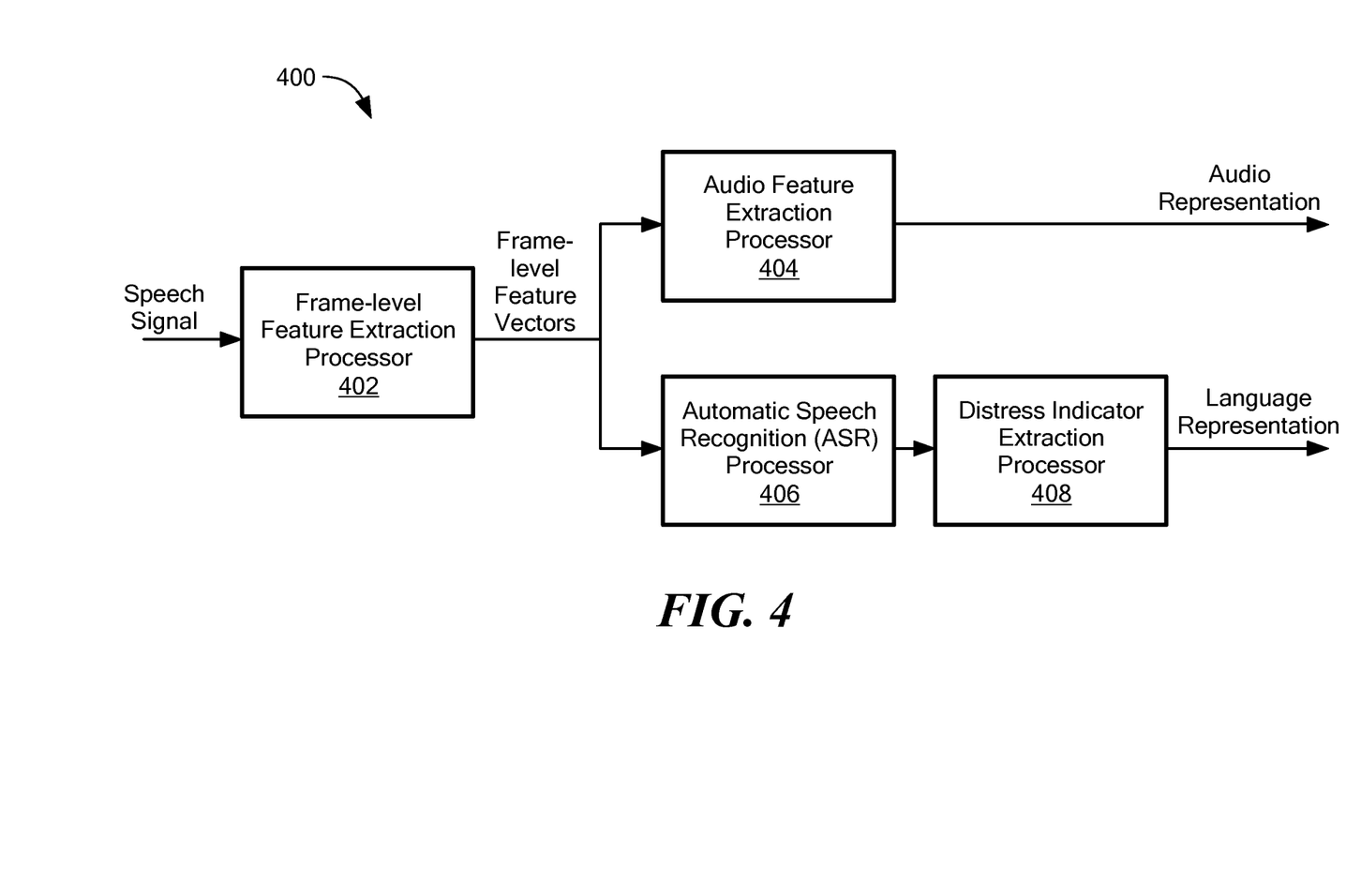
FIG. 4 is a block diagram showing a system for generating a speech representation using a combination of audio and language descriptors extracted from spoken responses.

In a particular embodiment, a feature extractor processor 210 analyzes speech responses from training subjects 206 (e.g., via a microphone) and generates corresponding speech representations based on a combination of audio and language descriptors. An illustrative system for generating such speech representations is shown in FIG. 4 and described below.

In certain embodiments, a feature extractor processor 210 extracts relevant features from EEG response signals. The EEG signals are represented using a set of statistical functionals based on channel-specific spectral power coefficients over temporal sliding windows. More specifically, a subject's EEG response signal may be divided into segments temporally aligned with the stimuli (e.g., images presented on a computer display). Next, EEG decontamination processing is performed to identify and remove various artifact types, such as electromyography, eye blinks, excursions, saturations, and spikes. In addition, a band-pass filter may be applied to limit the signal to a pre-determined frequency range (e.g., between 3 and 45 Hz). Next, the decontaminated EEG signals may be arranged into multiple overlapping segments from which one or more features are extracted. Non-limiting examples of EEG features include: power in delta (3-5 Hz), theta (5-8 Hz), slow alpha (8-10 Hz), alpha (8-12 Hz), beta (12-30 Hz) and gamma (30+Hz) bands for each channel. Next, statistical functionals (e.g., mini-mum, maximum, range, mean, standard deviation, skewness, kurtosis, and mode) can be calculated for various spectral power coefficients over the segments corresponding to a single stimulus 204. The various feature vectors for the statistical functionals can be concatenated together to generate vector-based EEG feature representation data suitable for learning and/or training.

Although the stimuli 204 may be presented to the subject 206 in series (i.e., according to the protocol 202), the sensors 208 (to collect subject responses) and the corresponding feature extraction processors 210 can operate in parallel. For example, while a single image is displayed to the subject 206, EEG signals and audio-visual data can be collected and processed in parallel.

Feature representation data can be classified as either "low-cost" or "high-cost" based upon the type of stimuli, response collection protocol, sensors, and/or feature extraction techniques. As used herein, "low-cost" information refers to information that can be obtained ubiquitously among a general population in the field, whereas high-cost information may involve a complicated collection protocol applicable to a laboratory setting but difficult in the field. Although such a distinction is application specific, factors that may be used to distinguish high and low-cost information include: high-cost information may involve the use of relatively aversive stimuli and/or invasive sensors compared with those used to obtain low-cost information; and high-cost information may be associated with relatively longer detection times, more expensive and scarce testing equipment, greater level of skill required to administer the test, greater pain to the subject, etc. The computational cost of different feature extraction techniques could also be a factor of the "cost."

In a particular embodiment, low-cost information includes video and speech response to open-ended questions, whereas high-cost information includes neurophysiological signals (e.g., EEG signals) obtained from potentially aversive collection protocols (e.g., responses to negative image stimuli).

Figure 3:
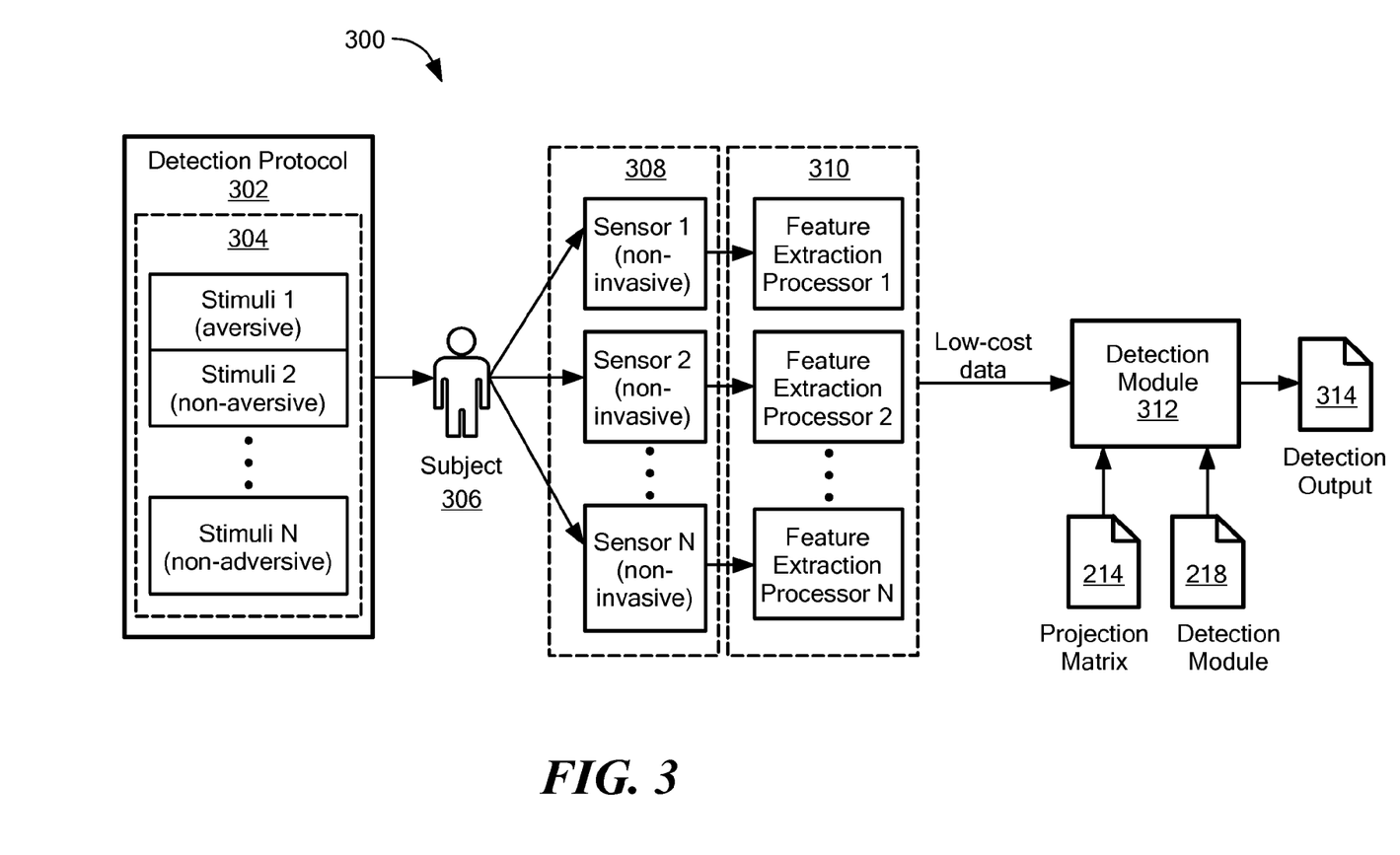
FIG. 3 is a block diagram showing an illustrative system for detecting psychological states using a multi-view model.

The relationship-learning module 212 receives high-cost and low-cost feature representation data from the feature extraction processors 210 and employs a suitable technique to learn a relationship therebetween. As output, the relationship-learning module 212 generates a projection matrix 214, which is used by the training module 216 and also by a detection module 312 (FIG. 3). In some embodiments, the relationship-learning module 212 uses a PLS method to solve linear systems equations involving multiple training samples, as described above. Accordingly, the training system 200 may include a training sample data store 220 to store (or "collect") feature representation data for a suitable number of samples to solve the bilinear system equations.

The training module 216 receives low-cost data from the feature extraction processors 210 and the projection matrix 214 from the relationship-learning module 212. In some embodiments, the feature representation data is stored within the training sample data store 220 and retrieved after the projection matrix is generated 214. The training module 216 uses the projection matrix 214 to project the low-cost data into a latent space where the detection model 218 is trained.

The training module 216 can use any suitable machine learning technique to train a detection model 218. In certain embodiments, the training module 216 uses a classifier technique, such as Gaussian Naive Bayes or Linear Support Vector Machine (SVM). In certain embodiments, the training module 216 uses supervised learning and, therefore, training samples may be labeled to inform the supervised training method. For example, prior to applying the protocol 202, training subjects 206 may be labeled as either in treatment for PTSD, negative for PTSD and high stress per the Holmes-Rahe MLS inventory, or negative for PTSD and low stress.

In some embodiments, the training system 200 approaches multi-label psychological state detection as multiple independent binary classification problems, with a separate one-versus-all SVM for each indicator. Thus, the relationship-learning module 212 and the training module 216 may generate N projection matrices and N detection models, respectively, one for each of the N psychological states.

As output, the training module 216 generates a trained detection model 218, which may be in any suitable form to apply by a detector. In some embodiments, the detection module 218 is a matrix.

Referring to FIG. 3, in which like elements of FIG. 2 are shown having like reference designators, an illustrative detection system 300 uses a multi-view detection model to detect psychological states. The detection system 300 includes feature extraction processors 310 operatively coupled to receive sensor data from one or more sensors 308, and a detection module 312 operatively coupled to receive feature representation data from the feature extraction processors 310. Stimuli 304 are presented/applied to a subject 306 according to a predetermined detection protocol 302; the subject's responses are detected, measured, recorded, or otherwise sensed by the sensors 308. In some embodiments, the detection system 300 includes non-aversive stimuli and non-invasive sensors, as shown. In a particular embodiment, the stimuli 304 comprise a short sequence of open-ended questions and imagery, and the sensors 308 comprise a microphone to capture speech responses.

The detection model 312 has access to the learned projection matrix 214 and trained detection model 218 generated by the training system 200 (FIG. 2). As described above, the detection model 218 is trained using low-cost data projected into a latent space using the projection matrix 214. Likewise, the detection model 312 receives low-cost feature representation data from the feature extraction processors 310, uses the projection matrix 214 to project the low-cost data to the same latent space, and applies the detection model 218 to the projected data, to generate detector output 314.

The detector output 314 may include any data suitable (provided in any practical format) to identify/diagnose psychological states. In certain embodiments, the detector model is a probabilistic classifier and the detector output 314 comprises one or more confidence levels (e.g., values in the range [0,1]) indicating a degree of certainty over one or more psychological states, given response data from the subject 306. For example, for detecting PTSD, the detector output 314 may comprise a stress level, which can be applied to the Holmes-Rahe scale to identify highly stressed individuals and, in turn, to diagnose PTSD. Alternatively, the detector model may use a binary classifier and, accordingly, the detection output 314 may include a binary value (e.g., 0 or 1), usually inferred according to an internal confidence value and a threshold value.

In certain embodiments, the detection system 300 (or portions thereof) are provided as a software application configured to run on a mobile device, such as a laptop computer, a tablet, a smartphone, or the like. In a certain embodiment, the detection system 300 includes a smartphone app to display non-aversive imagery and/or sequence of open-ended questions to elicit responses from a subject; speech responses can be collected using a built-in microphone, text responses can be collected using a touchscreen/keyboard, while a built-in camera can be used to capture images of the subject's facial expressions. Because mobile devices may have relatively little processing capability, portions of the feature extraction processing and/or detection module processing may be delegate to a centralized remote processor (e.g., via a network service). Advantageously, the projection matrix 214 and detection model 218 could be improved over time without requiring changes to the smartphone app.

In a particular embodiment, the detection system 300 is provided within a call center. Subjects 306 call into the call center and listen to a sequence of questions. Their spoken responses are captured and processed using the speech/language analysis techniques described above. The sequence of questions may be read by a human operator, or pre-recorded for automatic playback.

In some embodiments, the detection system 300 includes a device, or other means, to obtain remotely-generated sensor data corresponding to a subject's response to stimuli.

Considering the call-center example, the detection system may include a means to receive audio signals generated remotely (e.g., by a microphone, telephone, etc.) in response to the subject's speech. Any suitable data input device could be used within the detection system 300, including a plain old telephone service (POTS) receiver, a radio frequency (RF) receiver, a computer storage device, and/or a network receiver.

FIG. 4 illustrates a system 400 for extracting speech representations based on a combination of audio and language descriptors from spoken responses. The system 400 includes a frame-level feature extraction processor 402, an audio feature extraction processor 404, an automatic speech recognition (ASR) processor 406, and a distress indicator extraction processor 408, coupled together as shown. The system 400 may form a portion of the training system 200 (FIG. 2) and/or the detection system 300 (FIG. 3). For example, the system 400 may correspond to one or more of the feature extraction processors 210, 310.

The frame-level feature extraction processor 402 receives an audio signal as input and generates corresponding frame-level feature vectors. The audio signal may correspond to a test/training subject's spoken responses to open-ended questions, and may be received, for example, directly from a sensor (e.g., a microphone) or a storage device. The audio signal may correspond to an analog audio signal and/or digital audio data. To analyze the audio signal, the processor 402 can represent the audio signal of each response as a set of local descriptors (it will be understood that this is commonly referred to as a "bag-of-word" approach). Each descriptor is a vector composed of a base cepstral features and the corresponding signal energy, together with their first and second derivatives. In a particular embodiment, 14 base cepstral features are used, resulting in 45-dimension descriptors. The Mel-warped cepstral coefficients are extracted from overlapping frames of audio data. In a particular embodiment, each audio frame is about 29 milliseconds (ms) long and processed at a rate of 100 frames per second. Each speech segment may be normalized by the mean cepstrum and peak energy, removing long-term channel bias. In addition, each vector can be scaled and translated such that the coefficients have zero mean and unit variance.

The resulting vectors, referred to herein as frame-level feature vectors, are used in various ways: they serve as input to the audio feature extraction processor 404 and are used to construct a compact audio representation; and, they serve as input to the ASR processor 406 and are used to infer the speech content.

The audio feature extraction processor 404 derives the audio representation by fusing the frame-level feature vectors using an unsupervised i-vector representation. Similarity can be modeled in terms of the distance between the distributions of the frame-level feature vectors (i.e., the "local descriptors"). In some embodiments, the audio feature extraction processor 404 uses one or more of the i-vector methods described by N. Dehak et al. in "Front-end factor analysis for speaker verification," Audio, Speech, and Language Processing, IEEE Transactions on, vol. 19, no. 4, pp. 788-789, May 2011, which is incorporated herein by reference. For example, an i-vector method can be described according to the equation $$\phi = m + Tw,$$

where m is the general mean vector obtained by concatenating mean parameters in a Gaussian Mixture Model (GMM) trained using data from different classes; $\phi$ refers to the same parameters from a GMM, specific to the local descriptor distribution for one speech response; matrix T defines a total variance space that constrains these GMM parameters into a subspace preserving the most variance in the training data; and w is a low dimensional factor that observes a standard normal distribution $N(0;1)$, referred to as the i-vector, as it has a dimensionality between those of the local descriptors and all the GMM parameters. The resultant i-vector can be used in common similarity measures, e.g., dot product and cosine distance. The total variance matrix T is estimated directly using unlabeled audio. The total variance matrix is estimated using an expectation-maximization (EM) technique. In certain embodiments, the total variance matrix is estimated using the EM algorithm used to estimate the eigenvoice matrix in P. Kenny et al., "Eigenvoice modeling with sparse training data," Speech and Audio Processing, IEEE Transactions on, vol. 13, no. 3, pp. 345-354, May 2005, except that each audio file carries a unique label instead of the speaker label. In a particular embodiment, the GMM has 52 Gaussian components and the dimensionality of the factor w is 100.

The ASR processor 406 applies a large-vocabulary speech recognizer to the frame-level feature vectors to transcribe the speech responses. These transcripts are input to the distress indicator extraction processor 408, which extracts various psychological distress indicators. In various embodiments, 52 psychological distress indicators are extracted relating to Diagnostic and Statistical Manual of Mental Disorders, Fourth Edition, (DSM-IV) diagnostic criteria for PTSD. Indicators may be hierarchically organized into five categories: stress exposure (e.g., combat exposure, traumatic loss, and captivity), affect (e.g., anger, fear, and worthlessness), behavior (e.g., social isolation, sleep problems, and excessive drug use), cognition (e.g., intrusive thoughts and memories, homicidal ideation, and post-traumatic amnesia), and domains of impairment (e.g., legal problems, financial problems, and occupational impairment). The distress indicator extraction processor 408 can approach multi-label psychological state detection as multiple independent binary classification problems, with a separate one-versus-all SVM for each indicator. The binary classifiers are trained using a set of rich features: stemmed unigrams, normalized pronoun and punctuation counts, average sentence lengths, sentiment words from multiple categories (e.g., cognitive processes, social processes), domain phrases derived from annotator rationales, and idiom indication features by checking constituent input words and phrases against a lexicon of English idioms and figurative phrases. In a particular embodiment, a distress indicator extraction processor 408 outputs language representation as a 52-dimensional vector composed of the distress indicator confidences.

It will be appreciated that the audio and language representations described hereinabove can be used in a PTSD detection model.

Figure 5:
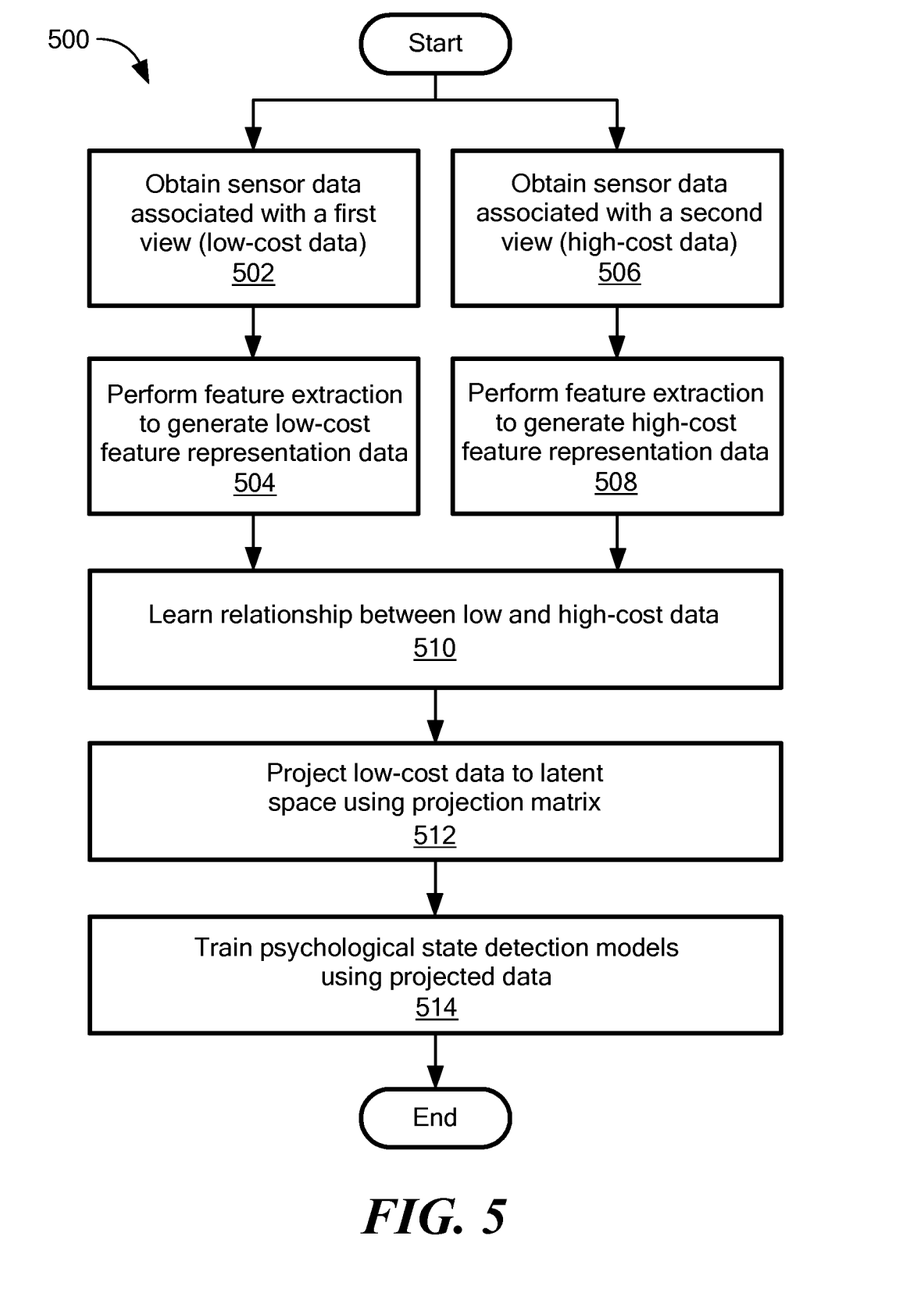
FIG. 5 is a flowchart showing an illustrative method for training a multi-view model for detecting psychological states.
Figure 6:
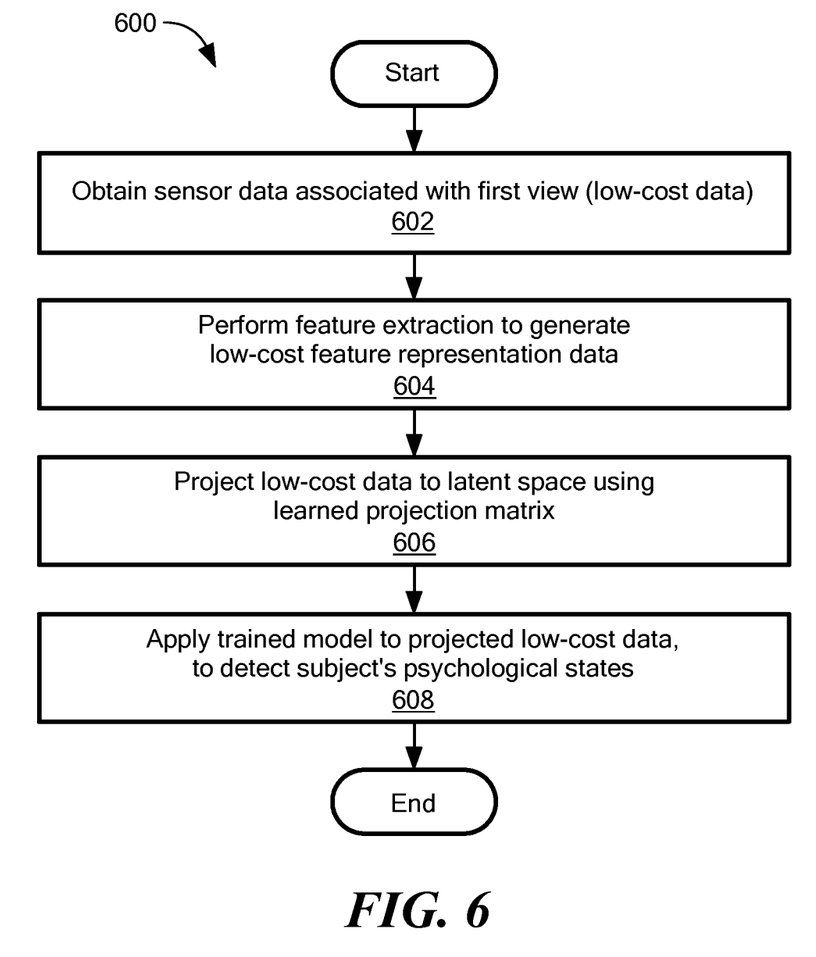
FIG. 6 is a flowchart showing an illustrative method for detecting psychological states using a multi-view model.

FIGS. 5 and 6 are flowcharts corresponding to the below contemplated techniques which could be implemented in the training system 200 (FIG. 2) and the detection system 300 (FIG. 3), respectively. Rectangular elements (typified by element 502 in FIG. 5), herein denoted "processing blocks," represent computer software instructions or groups of instructions. Alternatively, the processing blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of blocks described is illustrative only and can be varied without departing from the spirit of the concepts, structures, and techniques sought to be protected herein. Thus, unless otherwise stated the blocks described below are unordered meaning that, when possible, the functions represented by the blocks can be performed in any convenient or desirable order.

FIG. 5 shows an illustrative method 500 which may correspond to processing performed within the training system 200 of FIG. 2. At block 502, sensor data associated with a first (or "low-cost") view is obtained and, at block 504, feature extraction is performed to generate low-cost feature representation data. At block 506, sensor data associated with a second (or "high-cost") view is obtained and, at block 508, feature extraction is performed to generate high-cost feature representation data. It will be appreciated that the processing of blocks 506, 508 can be performed in parallel with the processing of blocks 502, 504.

At block 510, a projection matrix is learned to project the first feature representation to a latent space related to the first and second views (e.g., using a PLS method). At block 512, the low-cost feature representation data is projected into the latent space using the projection matrix and, at block 514, a psychological user state detection model is trained using the projected low-cost data. One or more of the processing steps 502-514 can be repeated to refine/improve the learned projection matrix and the trained detection model.

FIG. 6 shows an illustrative method 600 which may correspond to processing performed within the detection system 300 of FIG. 3. As input, the method 600 uses the projection matrix and the detection model learned/trained in method 500 of FIG. 5. At block 602, sensor data associated with the low-cost view is obtained and, at block 604, feature extraction is performed to generate low-cost feature representation data. At block 606, the low-cost feature representation data is projected into the latent space using the projection matrix and, at block 608, the trained detection model is applied to the projected low-cost data to detect the subject's psychological states.

Figure 7:
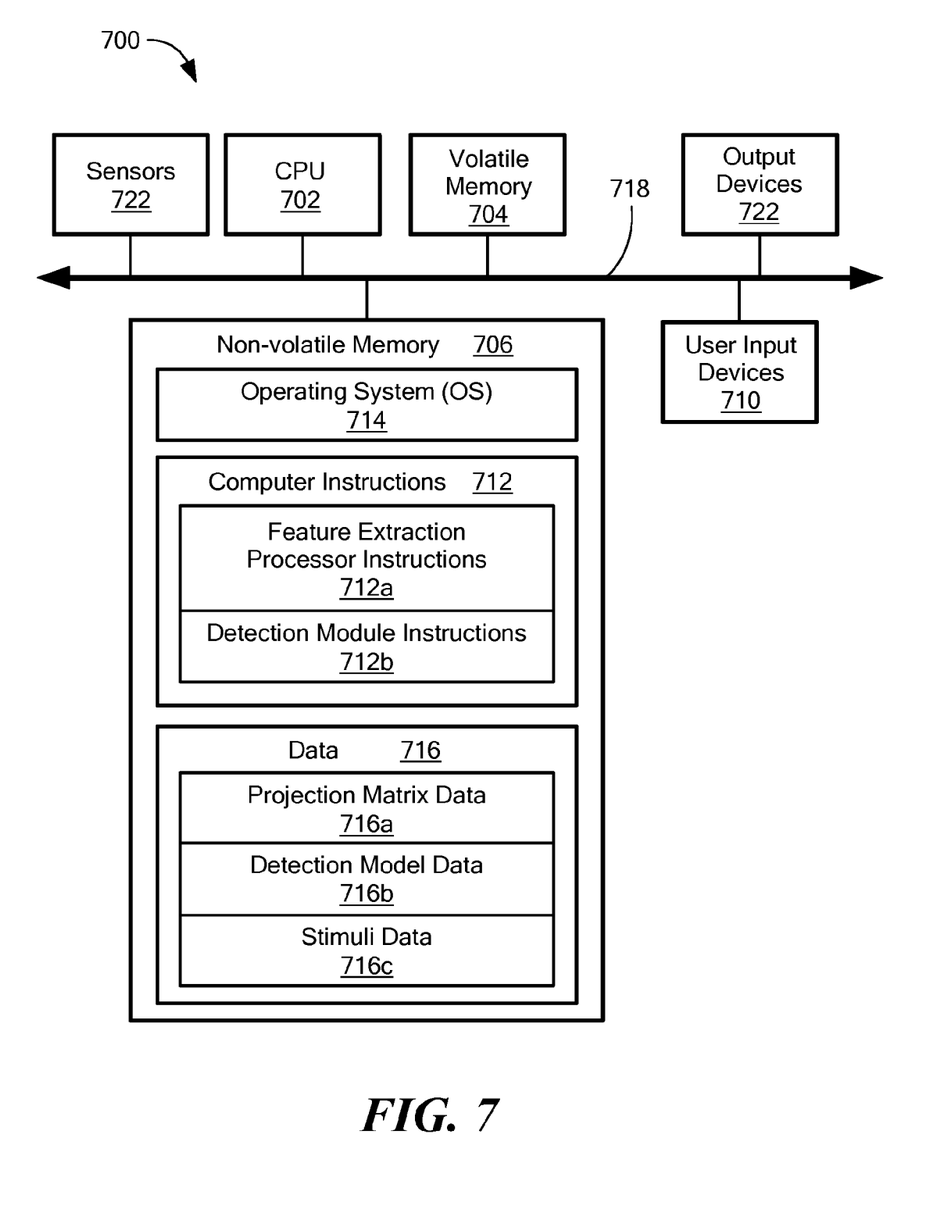
FIG. 7 is a schematic representation of an illustrative computer for use with the systems and methods of FIGS. 1-6.

FIG. 7 shows an illustrative computer or other processing device 700 that can perform at least part of the processing described herein. The computer 700 can include a processor 702, a volatile memory 704, a non-volatile memory 706 (e.g., hard disk or flash device), output devices 708, user input devices 710, and sensors 722, coupled together by a bus 718. Non-limiting examples of output devices 708 include computer displays and speakers. Non-limiting examples of user input devices 710 include mice, keyboards, and touchscreen devices. The sensors 722 may be the same as or similar to any of the sensors 208 and the sensors 308 described above in conjunction with FIGS. 2 and 3, respectively. As described above, a user input device 710 could also be used as a sensor 722.

The non-volatile memory 706 can store computer instructions 712, an operating system 714, and data 716. In one example, the computer instructions 712 are executed by the processor 702 out of volatile memory 704. In some embodiments, the computer instructions 712 include feature extraction processor instructions 712a and detection module instructions 712b to implement a feature extraction processor 310 (FIG. 3) and a detection module 312 (FIG. 3), respectively. In certain embodiments, the data 716 includes projection matrix data 716a corresponding to a projection matrix 214 (FIG. 2), detection model data 716b corresponding to a detection model 218 (FIG. 2), and stimuli data 716c (e.g., audio-visual content) corresponding to stimuli 208 (FIG. 2) and/or stimuli 308 (FIG. 3).

Processing may be implemented in hardware, software, or a combination of the two. In embodiments, processing is provided by computer programs executing on programmable computers/machines that each includes a processor, a storage medium or other article of manufacture that is readable by the processor (including volatile and non-volatile memory and/or storage elements), at least one input device, and one or more output devices. Program code may be applied to data entered using an input device to perform processing and to generate output information.

The system can perform processing, at least in part, via a computer program product, (e.g., in a machine-readable storage device), for execution by, or to control the operation of, data processing apparatus (e.g., a programmable processor, a computer, or multiple computers). Each such program may be implemented in a high level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer. Processing may also be implemented as a machine-readable storage medium, configured with a computer program, where upon execution, instructions in the computer program cause the computer to operate.

Processing may be performed by one or more programmable processors executing one or more computer programs to perform the functions of the system. All or part of the system may be implemented as special purpose logic circuitry (e.g., an FPGA (field programmable gate array) and/or an ASIC (application-specific integrated circuit)).

All references cited herein are hereby incorporated herein by reference in their entirety.

Having described certain embodiments, which serve to illustrate various concepts, structures, and techniques sought to be protected herein, it will be apparent to those of ordinary skill in the art that other embodiments incorporating these concepts, structures, and techniques may be used. Accordingly, it is submitted that that scope of the patent should not be limited to the described embodiments but rather should be limited only by the spirit and scope of the following claims.

What is claimed is:

1. A system for detecting psychological states, the system comprising:
   a device to obtain sensor data corresponding to a subject's response to stimuli;
   a feature extraction processor to extract one or more features from the sensor data to generate feature representation data, the feature representation data being associated with a first view;
   a memory device configured to store a projection matrix modeling a relationship between the first view and a second view, and to store a detection model trained using training data associated with the first view transformed to a latent space using the projection matrix, wherein the first view is associated with low-cost data and the second view is associated with high-cost data; and
   a detection module to transform the feature representation data to the latent space using the projection matrix, and to apply the transformed feature representation data to the detection model to detect one or more psychological states of the subject,
   wherein the device to obtain sensor data comprises a first device to obtain first sensor data corresponding to a training subject's response to the stimuli and a second device to obtain second sensor data corresponding to the training subject's response to the stimuli, wherein the feature extraction processor is a first feature extraction processor, wherein the feature representation data is first feature representation data, the system further comprising:
   a second feature extraction processor to extract one or more features from the second sensor data to generate second feature representation data, the second feature representation data being associated with the second view;
   a relationship learning module to receive the first and second feature representation data and to learn the projection matrix for projecting the first feature representation to the latent space related to the first and second views; and
   a training module to transform the first feature representation data to the latent space using the projection matrix, and to train the detection model using the transformed feature representation data.

2. The system of claim 1 wherein the one or more psychological states include post-traumatic stress disorder (PTSD) indicators.

3. The system of claim 1 wherein the sensor data comprises audio signal data responsive to the subject's speech.

4. The system of claim 3 wherein the feature representation data comprises an audio representation and a language representation.

5. The system of claim 4 wherein the feature extraction processor comprises:
   a frame-level feature extraction processor to receive the audio signal data and to generate frame-level feature vectors;
   an audio feature extraction processor to generate the audio representation using the frame-level feature vectors;
   an automatic speech recognition (ASR) processor to apply a speech recognizer to the frame-level feature vectors to transcribe the subject's speech; and
   a distress indicator extraction processor to extract psychological distress indicators from the transcribed subject's speech to generate the language representation.

6. The system of claim 1 wherein the second view is associated with psychophysiological data.

7. The system of claim 6 wherein the psychophysiological data comprises electroencephalography (EEG) data.

8. The system of claim 1 wherein the stimuli include images stored upon a non-volatile memory, the system further comprising a computer display to display the images.

9. The system of claim 1 wherein the projection matrix comprises a bilinear factor model selected to maximize the covariance between the first and second views.

10. The system of claim 1 wherein the first sensor data comprises audio signal data and the second sensor data comprises psychophysiological data.

11. A method for detecting psychological states, the method comprising:
   obtaining sensor data associated with a first view, the sensor data corresponding to a subject's response to stimuli;
   performing feature extraction to generate feature representation data, a projection matrix modeling a relationship between the first view and a second view, wherein the first view is associated with low-cost data and the second view is associated with high-cost data;

transforming the feature representation data to a latent space using the projection matrix; and applying a detection model to the transformed feature representation data to detect one or more psychological states of the subject, wherein obtaining sensor data associated with a first view comprises obtaining first sensor data using a first device, the first sensor data corresponding to a training subject's response to the stimuli, wherein the feature representation data is first feature representation data, and obtaining second sensor data using a second device, the second sensor data corresponding to the training subject's response to the stimuli, the method further comprising:

performing feature extraction on the first sensor data to generate first feature representation data, the first feature representation data being associated with the first view:

performing feature extraction on the second sensor data to generate second feature representation data, the second feature representation data being associated with a second view;

learning the projection matrix using the first and second feature representation data;

transforming the first feature representation data to the latent space using the projection matrix; and training the detection model using the transformed first feature representation data.

12. The method of claim 11 wherein applying a detection model to the transformed feature representation data to detect one or more psychological states of the subject comprises detecting post-traumatic stress disorder (PTSD) indicators.

13. The method of claim 11 wherein obtaining sensor data associated with a first view comprises obtaining audio signal data via a microphone.

14. The method of claim 13 wherein the audio signal data is responsive to the subject's speech and wherein performing feature extraction comprises:

receiving the audio signal data;

generating frame-level feature vectors;

generating an audio representation using the frame-level feature vectors;

applying an automatic speech recognition (ASR) to the frame-level feature vectors to transcribe the subject's speech; and extracting psychological distress indicators from the transcribed subject's speech to generate a language representation.

15. The method of claim 11 wherein the second view is associated with psychophysiological data.

16. The method of claim 15 wherein the psychophysiological data includes electroencephalography (EEG) data.

17. The method of claim 11 further comprising displaying images upon a computer display to elicit the subjects' response.

* * * * *